(12) United States Patent
Ogasawara

(10) Patent No.: US 6,495,725 B2
(45) Date of Patent: Dec. 17, 2002

(54) PROCESS FOR THE PREPARATION OF OPTICALLY ACTIVE ENONES AND INTERMEDIATES THEREOF

(75) Inventor: Kunio Ogasawara, Sendai (JP)

(73) Assignee: Chisso Corporation, Osaka (JP)

( * ) Notice: Subject to any disclaimer, the term of this patent is extended or adjusted under 35 U.S.C. 154(b) by 81 days.

(21) Appl. No.: 09/736,141

(22) Filed: Dec. 15, 2000

(65) Prior Publication Data

US 2002/0028958 A1 Mar. 7, 2002

(30) Foreign Application Priority Data

Dec. 22, 1999 (JP) ............................................ 11-364179
Oct. 6, 2000 (JP) ...................................... 2000-307209

(51) Int. Cl.$^7$ ............................................. C07C 45/00
(52) U.S. Cl. ...................... 568/338; 568/379; 568/591; 568/673; 568/838; 560/121; 562/503; 549/436
(58) Field of Search ........................ 560/121; 549/436; 562/503; 568/379, 338, 591, 673, 838

(56) References Cited

U.S. PATENT DOCUMENTS 4,873,360 A 10/1989 Johnson et al. .............. 560/121

OTHER PUBLICATIONS

Leroy et al, Organic Letters, 1(5), 775–777 (1999).*
Chiara et al, Tetrahedron Letters, 32(9), 1125–8 (1991).*
A. Armstrong, et al., Tetrahedron: Asymmetry, vol. 8, No. 10, pp. 1677–1684, "Concise Synthesis of (4S,5S)–4, 5–(Isopropylidenedioxy)–2–Cyclopentenone and a Novel $C_2$–Symmetric Ketone," 1997.
C–C. Lin, et al., J. Org. Chem., vol. 62, No. 12, pp. 3806–3807, "Novel Asymmetric Route to Carbanucleoside and Prostanoid Intermediates: Efficient Preparation of Both Optical Antipodes of Chiral Cyclopentenone.," 1997.
H. Sano, et al., Tetrahedron: Asymmetry, vol. 6, No. 5, pp. 1143–1150, "Synthesis of an Optically Active Corbocyclic Derivative of (+)–Hydantocidin,"1995.
P. PM.A. Dols, et al., Tetrahedron, vol. 50, No. 28, pp. 8515–8538, "4–Hydroxycyclopent–2–EN–1–One and Derivatives as Chiral Synthetic Equivalents of Cyclopentadienone in Asymmetric Diels–Alder Reactions," 1994.
H.J. Bestmann, et al., Synlett, vol. 12, pp. 751–753, "Total Synthesis of (–) –Aristeromycin," 1990.
S. M. Ali, et al., Tetrahedron Letters, vol. 31, No. 11, pp. 1509–1512, "Efficient Enantioselective Syntheses of Carbocyclic Nucleoside and Prostaglandin Synthons," 1990.
C. J. Flann et al., Synthetic Communications, vol. 18, No. 4, pp. 391–402, "Homochiral Ketals in Organic Synthesis. Enantioselective Synthesis of (4S,5S)–4, 5–Dihydroxycyclopent–2–EN–1–One Isopropylidine Ketal," 1988.
Carl R. Johnson, et al., "Triply Convergent Synthesis of (–)–Prostaglandin E$_2$," Journal of the American Chemical Society, 108, 1986, pp. 5655–5656.
Hiromi Nakashima, et al., "Chiral Preparation of Polyoxygenated Cyclopentanoids," Journal of Synthetic Organic Chemistry, No. 6, 2000, pp. 817–823.
Hiromi Nakashima, et al., Lipase–Mediated Resolution of cis–4–Cumyloxy–2–Cyclopenten–1–ol and its Utilization for Enantioconvergent Preparation of (–)–Oxabicyclo[3.3.0]–oct–6–en–3–one, Synlett, No. 11, 1999, pp. 1754–1756.
Hiromi Nakashima, et al., "An Enantiodivergent Route to α–Cuparenone Utilizing Chiral Cyclopentenol Having a Latent Meso Structure," The International Journal for the Rapid Publication of Preliminary Communications in Organic Chemistry, vol. 41, No. 15, Apr. 8, 2000, pp. 2639–2642.

* cited by examiner

Primary Examiner—Sreeni Padmanabhan
(74) Attorney, Agent, or Firm—Oblon, Spivak, McClelland, Maier & Neustadt, P.C.

(57) ABSTRACT

The present invention provides a simplified and convenient process for the preparation of an optically active enone such as 7,7-dimethyl-6,8-dioxabicyclo-[3,3,0]oct-3-en-2-one.

The invention further provides novel optically active intermediate compounds.

The process for the preparation of an optically active enone represented by the formula (4) comprises steps of (A) deprotecting the protecting group for the hydroxyl group at the 1-position in a compound represented by the formula (1) to a hydroxyl group (compound (2)), (B) oxidizing the hydroxyl group to a ketone group (compound (3)) and (C) deprotecting the protecting group for the hydroxyl group at the 4-position to form a double bond between the carbon atom at the 4-position and the carbon atom at the 5-position, according to the following reaction schemes:

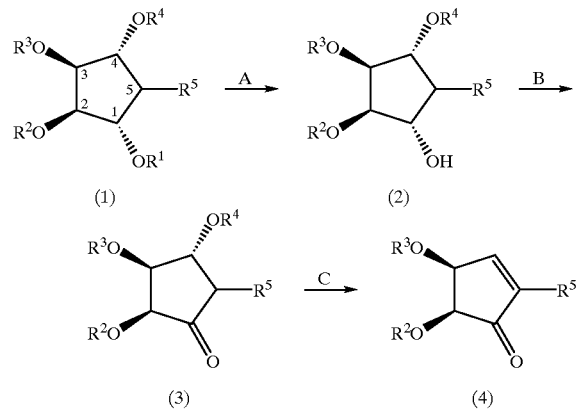

wherein $R^1$ and $R^4$ independently represent a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, $R^2$ and $R^3$ jointly represent acetonide, methyl ethyl ketal or diethyl ketal, and $R^5$ represents a hydrogen atom, an alkyl group having not more than 20 carbon atoms or a phenyl group.

18 Claims, No Drawings

PROCESS FOR THE PREPARATION OF OPTICALLY ACTIVE ENONES AND INTERMEDIATES THEREOF

FIELD OF THE INVENTION

This invention relates to a novel optically active enone derivative, which is a useful intermediate for natural products such as prostagrandins and drugs, processes for the preparation thereof and a novel optically active compound as intermediates.

BACKGROUND OF THE INVENTION

Recently, chiral alcohols with a plurality of hydroxyl groups have found wide and versatile utility as both enantiomers in the synthesis of optically active natural products or drugs and have become a focus of interest. In particular, the hydroxyl-protected enone form, i.e., 7,7-dimethyl-6,8-dioxabicyclo[3,3,0]oct-3-en-2-one, has been used as important building blocks for the synthesis of a variety of physiologically active substances such as prostagrandins.

Johnson et al. have accomplished a total synthesis of prostagrandin $E_2$ from optically active 7,7-dimethyl-6,8-dioxabicyclo[3,3,0]oct-3-en-2-one (J. Am. Chem. Soc., 1986, 108, 5655). According to this process, the optically active enone was synthesized by optical resolution of the racemate with (+)-N,S-dimethyl-S-phenylsulfoximine. However, imine as a resolving agent is expensive, and the resolution according to the process should be made after addition of imine by conducting the reaction at a low temperature of −78° C. Moreover, the process requires a reaction to regenerate a carbonyl group after resolution, which cannot always be easily carried out in an industrial scale. Thus, there has been a demand for a more simplified and convenient process for the preparation of an optically active enone, such as 7,7-dimethyl-6,8-dioxabicyclo[3,3,0]oct-3-en-2-one.

SUMMARY OF THE INVENTION

An object of the invention is to provide a more simplified process for the preparation of an optically active enone, such as 7,7-dimethyl-6,8-dioxabicyclo[3,3,0]-oct-3-en-2-one.

Another object of the invention is to provide intermediates obtainable during the process according to the invention.

Further object of the invention is to provide a novel optically active enone.

DETAILED DESCRIPTION OF THE INVENTION

We have found a simplified and efficient process for the preparation of both enantiomers of an optically active enone, for example, 7,7-dimethyl-6,8-dioxabicyclo[3,3,0]oct-3-ene-2-one, starting an optically active alcohol derivative represented by the formula (9).

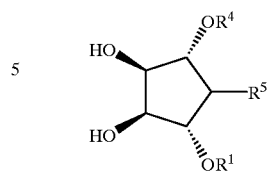

(9)

wherein $R^1$, $R^4$ and $R^5$ are as defined below.

Moreover, we have found that the intermediate obtained in the said process is a novel optically active compound, which is also useful chiral building blocks like the end product, i.e., optically active enone. The invention has been completed upon the above findings.

More specifically, as illustrated in Scheme 1 below, the present invention provides a process for the preparation of an optically active enone represented by the formula (4), which comprises steps of (A) deprotecting the protecting group for the hydroxyl group at the 1-position in a compound represented by the formula (1) to a hydroxyl group (compound (2)), (B) oxidizing the hydroxyl group to a ketone group (compound (3)) and (C) deprotecting the protecting group for the hydroxyl group at the 4-position to form a double bond between the carbon atom at the 4-position and the carbon atom at the 5-position to prepare the desired enone. Here all chemical names are referred to in accordance with the IUPAC nomenclature. For convenience sake, however, the position of a functional group shall be represented in accordance with the numbering as shown in the formula (1).

Scheme 1

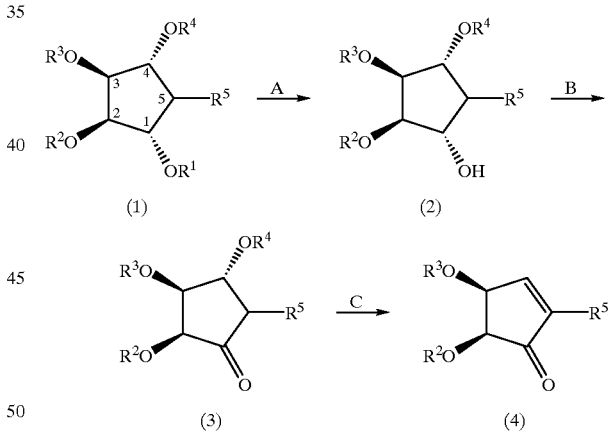

wherein $R^1$ and $R^4$ independently represent a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, $R^2$ and $R^3$ jointly represent acetonide, methyl ethyl ketal or diethyl ketal, and $R^5$ represents a hydrogen atom, an alkyl group having not more than 20 carbon atoms or a phenyl group.

Also, as illustrated in Scheme 2 below, the invention provides a process for the preparation of an optically active enone represented by the formula (7), which comprises the steps of (A') deprotecting the protecting group for the hydroxyl group at the 4-position in a compound represented by the formula (1) to a hydroxyl group (compound (5)), (B') oxidizing the hydroxyl group to a ketone group (compound (6)) and (C') deprotecting the protecting group for the hydroxyl group at the 1-position to form a double bond between the carbon atom at the 1-position and the carbon atom at the 5-position to prepare the desired enone.

Scheme 2

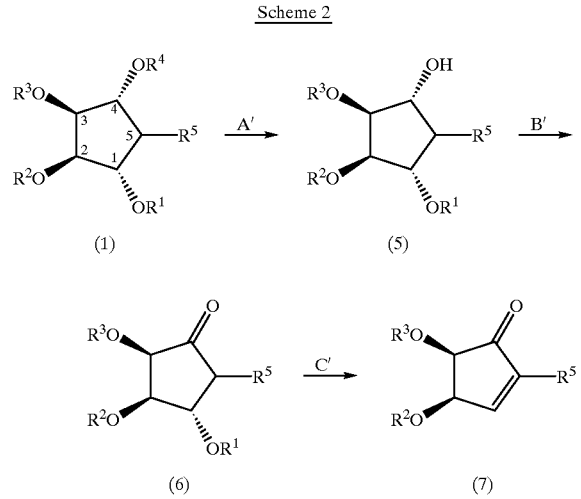

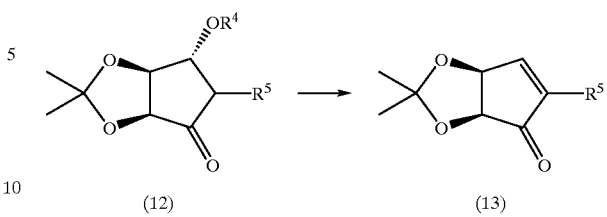

wherein $R^4$ and $R^5$ are as defined above.

Further, as illustrated in Scheme 4 below, the invention provides a process for the preparation of an optically active enone represented by the formula (16), which comprises the steps of deprotecting the protecting group for the hydroxyl group at the 4-position in a compound represented by the formula (10) wherein the protecting group at the 1-position is a cumyl group and the protecting groups at the 2- and 3-positions are acetonide to a hydroxyl group (compound (14)); oxidizing the hydroxyl group to a ketone group (compound (15)); and deprotecting the protecting group for the hydroxyl group at the 1-position to form a double bond between the carbon atom at the 1-position and the carbon atom at the 5-position to prepare the desired enone.

wherein $R^1$, $R^2$, $R^3$, $R^4$ and $R^5$ are as defined above.

Further, as illustrated in Scheme 3 below, the invention provides a process for the preparation of an optically active enone represented by the formula (13), which comprises the steps of deprotecting the protecting group for the hydroxyl group at the 1-position in a compound represented by the formula (10) wherein the protecting group at the 1-position is a cumyl group and the protecting groups at the 2- and 3-positions are acetonide to a hydroxyl group (compound (11)); oxidizing the hydroxyl group to a ketone group (compound (12)); and deprotecting the protecting group for the hydroxyl group at the 4-position to form a double bond between the carbon atom at the 4-position and the carbon atom at the 5-position to prepare the desired enone.

Scheme 4

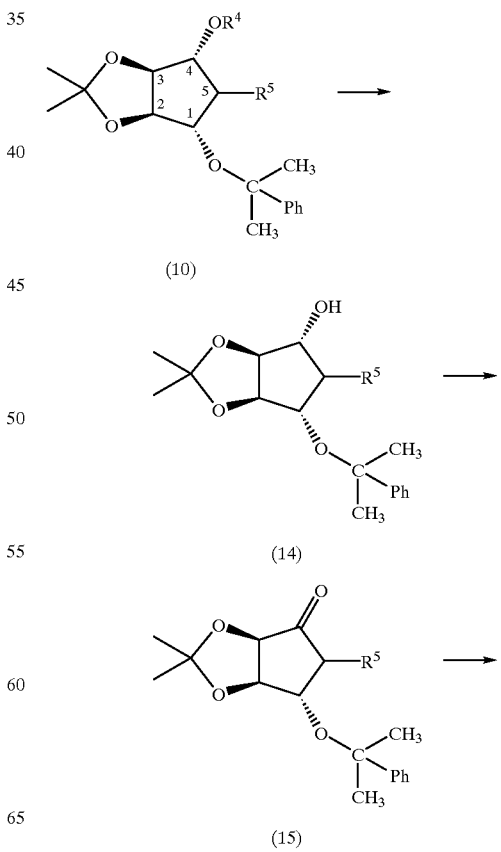

Scheme 3

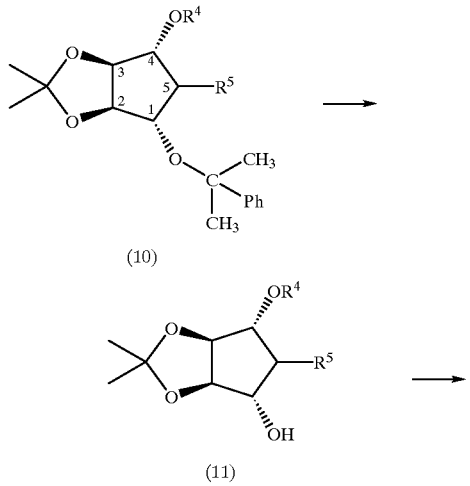

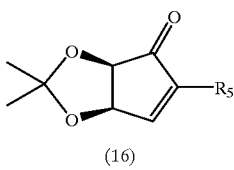

wherein $R^4$ and $R^5$ are as defined above.

Moreover, as illustrated in Scheme 5 below, the invention provides a process for the preparation of an optically active enone represented by the formula (16), which comprises the steps of deprotecting the protecting group for the hydroxyl group at the 4-position in a compound represented by the formula (17) wherein the protecting group at the 4-position is a cumyl group and the protecting groups at the 2- and 3-positions are acetonide to a hydroxyl group (compound (18)); oxidizing the hydroxyl group to a ketone group (compound (19)); and deprotecting the protecting group for the hydroxyl group at the 1-position to form a double bond between the carbon atom at the 1-position and the carbon atom at the 5-position to prepare the desired enone.

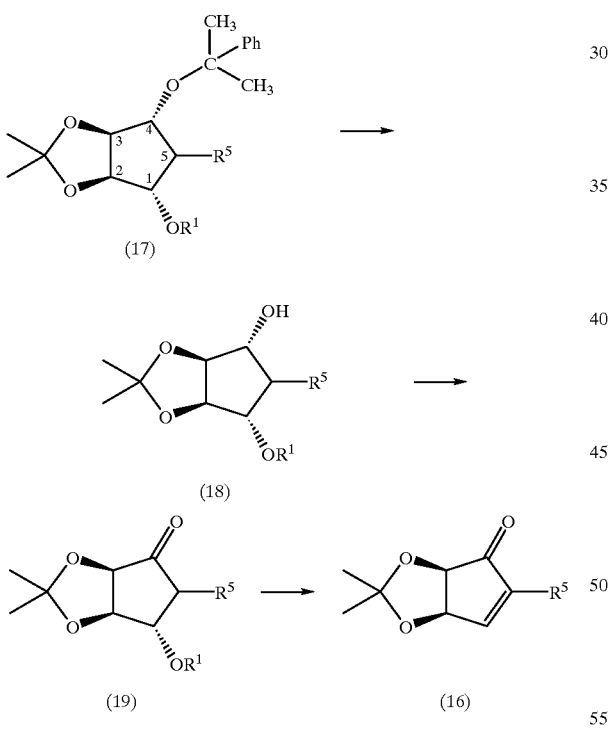

wherein $R^1$ and $R^5$ are as defined above.

Also, as illustrated in Scheme 6 below, the invention provides a process for the preparation of an optically active enone represented by the formula (13), which comprises the steps of deprotecting the protecting group for the hydroxyl group at the 1-position in a compound represented by the formula (17) wherein the protecting group at the 4-position is a cumyl group and the protecting groups at the 2- and 3-positions are acetonide to a hydroxyl group (compound (20)); oxidizing the hydroxyl group to a ketone group (compound (21)); and deprotecting the protecting group for the hydroxyl group at the 4-position to form a double bond between the carbon atom at the 4-position and the carbon atom at the 5-position to prepare the desired enone.

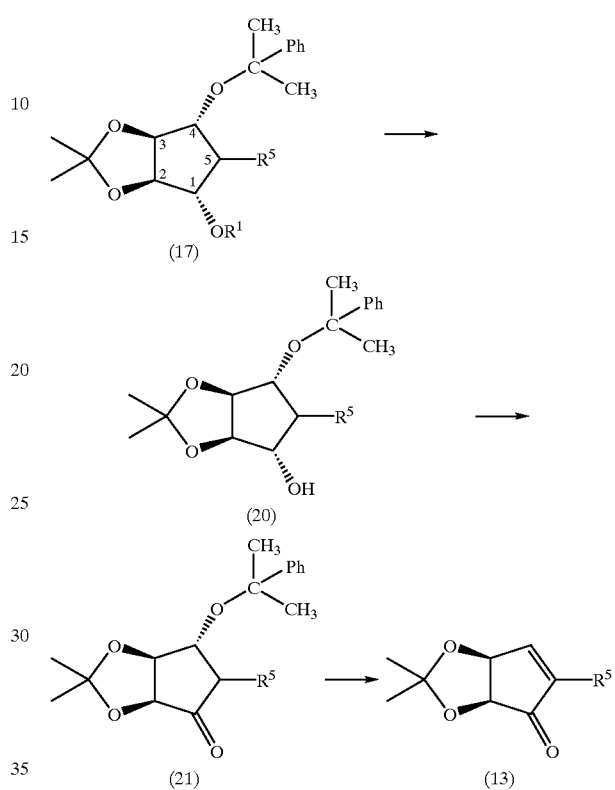

wherein $R^1$ and $R^5$ are as defined above.

Still further, the invention provides an optically active compound represented by the formula (1). The compounds represented by the formula (1) include enantiomers thereof.

The invention also provides optically active compounds represented by the formulae (2)–(7), (9)–(21) and (23)–(25) as illustrated in the below-mentioned Schemes.

The present invention will be explained below in more detail.

The process for the preparation of an optically active enone according to this invention comprises the step A or A' wherein the protecting group at the 1-position or the 4-position in a compound represented by the formula (1) is deprotected, the step B or B' wherein the deprotected hydroxyl group is oxidized to a ketone group, and the step C or step C' wherein the protecting group at the 4-position or the 1-position is deprotected followed by dehydration to form a double bond, as illustrated by the following Scheme 7. In this case, it may be feasible to selectively synthesize any enantiomer by first deprotecting either of the hydroxyl groups.

Scheme 7

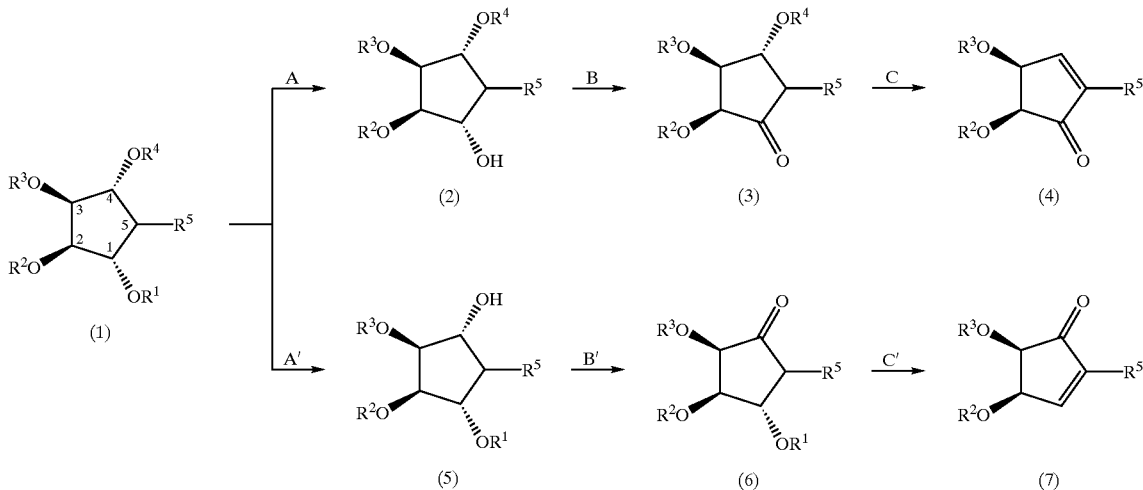

More specifically, the upper route in Scheme 7 comprising the steps A, B and C, wherein the protecting group at the 1-position in the compound (1) is first deprotected, can selectively produce the optically active enone represented by the formula (4), whereas the lower route comprising the step A', B' and C', wherein the protecting group at the 4-position in the compound (1) is first deprotected, can selectively produce an enantiomer of the optically active enone represented by the formula (4), as shown by the formula (7). When the protecting groups $R^2$ and $R^3$ form acetonide and the protecting group $R^5$ is a hydrogen atom, the dextro-rotatory compound represented by the formula (37), (+)-7,7-dimethyl-6,8-dioxabicyclo[3,3,0]-oct-3-en-2-one, is obtained according to the upper route in Scheme 7. On the other hand, the levo-rotatory compound represented by the formula (40), (−)-7,7-dimethyl-6,8-dioxabicyclo[3,3,0]oct-3-en-2-one, is obtained according to the lower route.

As already mentioned, the compounds represented by the formula (1) may include enantiomers thereof. Thus, all optically active compounds prepared using the compound of the formula (1) as a starting material may also include enantiomers thereof. In short, when the enantiomer of the compound represented by the formula (1) is used as a starting material, whose protecting groups $R^2$ and $R^3$ form acetonide and protecting group $R^5$ is a hydrogen atom, the levo-rotatory compound represented by the formula (40), (−)-7,7-dimethyl-6,8-dioxabicyclo[3,3,0]-oct-3-en-2-one, is obtained according to the upper route in Scheme 7. On the other hand, the dextro-rotatory compound represented by the formula (37), (+)-7,7-dimethyl-6,8-dioxabicyclo[3,3,0]oct-3-en-2-one, is obtained according to the lower route.

In other words, any enantiomer may be selectively synthesized depending on the chirality of the starting optically active compound and the hydroxyl group to be first deprotected.

The optically active enone, which may be prepared according to the process of this invention, is the compounds represented by the formulae (4) and (7), respectively, wherein $R^2$, $R^3$ and $R^4$ are within the scope mentioned below.

The protecting groups $R^2$ and $R^3$ for a hydroxyl group in the invention may be any of those groups that may act as a protecting group for a hydroxyl group and could not be eliminated by the deprotection reaction for the protecting group $R^1$ or $R^4$. The protecting groups $R^2$ and $R^3$ may be independent each other, and they may be joined together with the carbon atoms at the 2-position and the 3-position in the cyclopentane ring to form a ring.

Preferably, the protecting groups $R^2$ and $R^3$ are joined together, such as methyl ethyl ketal, diethyl ketal and acetonide, acetonide being more preferable.

The group $R^5$ in the present invention is any of those functional groups that do not inhibit the reactions according to the invention. Preferably, it may be a hydrogen atom, an alkyl group or a phenyl group. A hydrogen atom and an alkyl group of 20 or less carbon atoms are particularly preferred.

The compound represented by the formula (1), which is a starting material in the process for the preparation of an optically active enone according to the invention, has the following characteristics. $R^2$, $R^3$ and $R^5$ in the formula (1) are within the same scope as defined above.

The protecting groups $R^1$ and $R^4$ for a hydroxyl group in the invention may be any of those groups that may act as a protecting group for a hydroxyl group. Preferably, there may be mentioned ether-type protecting groups, silyl ether-type protecting groups and ester-type protecting groups. The ether-type protecting groups may include, for example, methoxymethyl, t-butylthiomethyl, t-butoxymethyl, siloxymethyl, 2,2,2-trichloroethoxymethyl, 2-(trimethylsilyl)ethoxymethyl, tetrahydropyranyl, tetrahydrofuranyl, 1-ethoxyethyl, 1-methyl-1-methoxyethyl, 2,2,2-trichloroethyl, 2-trimethylsilylethyl, t-butyl, allyl, benzyl, p-methoxybenzyl, nitrobenzyl, cumyl group, α,α-diethylbenzyl, α-methyl-α-ethylbenzyl and α,α-dimethyl-p-methoxybenzyl. The silyl ether-type protecting groups may include, for example, trimethylsilyl, triethylsilyl, triisopropylsilyl, isopropyldimethylsilyl, ethyldimethylsilyl, and t-butyldimethylsilyl. The ester-type protecting groups may include, for example, acetyl, chloroacetyl, dichloroacetyl, trichloroacetyl, trifluoroacetyl, methoxyacetyl, pivaloyl or benzoyl. Of these groups, the ether-type and silyl ether-type protecting groups are preferable and cumyl group, α,α-diethylbenzyl, α,α-dimethyl-p-methoxybenzyl or t-butyldimethylsilyl is more preferable.

The protecting group $R^1$ in the present invention is not deprotected by the deprotection reaction for the protecting groups R⁴ and is deprotected selectively by the deprotection reaction for R¹, and the protecting group R⁴ is not deprotected by the deprotection reaction for the protecting group R¹ and is deprotected selectively by the deprotection reaction for R⁴.

For instance, the ether-type protecting group may be deprotected by hydrogenolysis, the silyl ether-type protecting group may be deprotected by alcoholysis under basic condition, and the ester-type protecting group may be deprotected under condition of potassium carbonate-alcohol. When R² and R³ form acetonide, which may be deprotected under acidic condition, the above parameters may be satisfied by selecting R¹ and R⁴ from the above-mentioned ether-type, silyl ether-type and ester-type protecting groups.

Illustrative are the following Schemes 8–11:

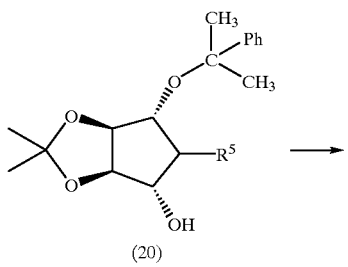
(20)

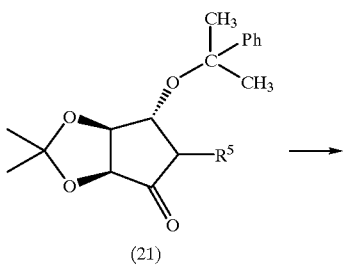
(21)

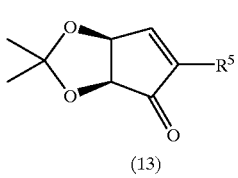
(13)

In these Schemes, R⁵ is as defined above.

Synthesis of the compounds represented by the formulae (26) and (27), which may be used as a starting material, is illustrated by the following Schemes 12 and 13, respectively.

Scheme 12

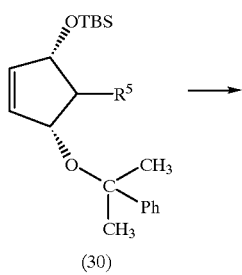
(30)

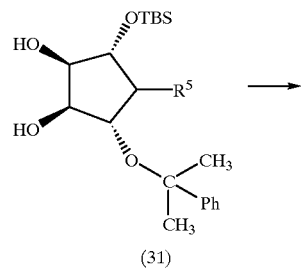
(31)

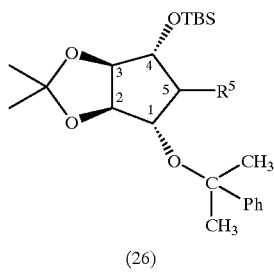
(26)

Scheme 13

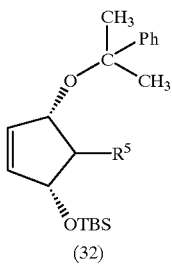
(32)

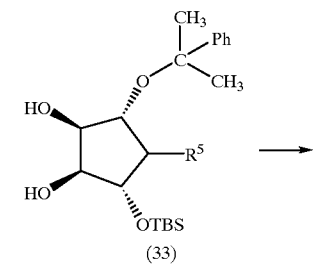
(33)

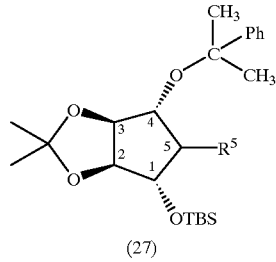
(27)

In these Schemes, R⁵ is as defined above.

According to the upper route in the aforementioned Scheme 7, the optically active enone represented by the formula (4) may be prepared starting from the compound represented by the formula (1) through the step A, the step B and the step C. Each of these steps will be explained later.

Process for the preparation of the compound (1) in Scheme 7

As illustrated in Scheme 14 below, the optically active compound (1) is prepared starting from a cyclopentene derivative (8), via a cyclopentanediol derivative (9) and subsequent protection of the diol.

Scheme 14

(8)

(9)

(1)

The reaction for preparing the cyclopentanediol derivative (9) from the cyclopenetene derivative (8) (wherein $R^1$, $R^4$ and $R^5$ are as defined above) may be carried out using any well-known oxidation reaction for cis-addition, and manganese oxidation and osmium oxidation are preferable. Osmium oxidation is particularly preferable.

The compound represented by the formula (8) may be prepared by reacting cyclopentadiene with cumene peroxide and $Cu(OAc)_2$, converting OAc to OH according to our method (Synthesis, 2000, 6, 817), oxidizing a hydroxyl group to a ketone group using as a catalyst manganese oxide in a mixed solvent of dichloromethane/hexane (1/5), reducing the ketone with $NaBH_4$ and finally protecting a hydroxyl group with another protecting group. The cumyl group may be deprotected and then replaced with another protecting group.

As illustrated in Schemes 15 and 16, the compound (10) or (17) may be prepared, for example, by osmium oxidation of the cyclopentene derivative (8) wherein $R^1$ is a cumyl group (compound (22)) or the cyclopentene derivative (8) wherein $R^4$ is a cumyl group (compound (24)), to form the 2,3-diol compound represented by the formula (23) or (25) and protecting hydroxyl groups with acetonide by reacting the diol compound with acetal dimethyl ketal.

Scheme 15

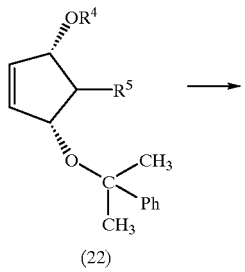

(22)

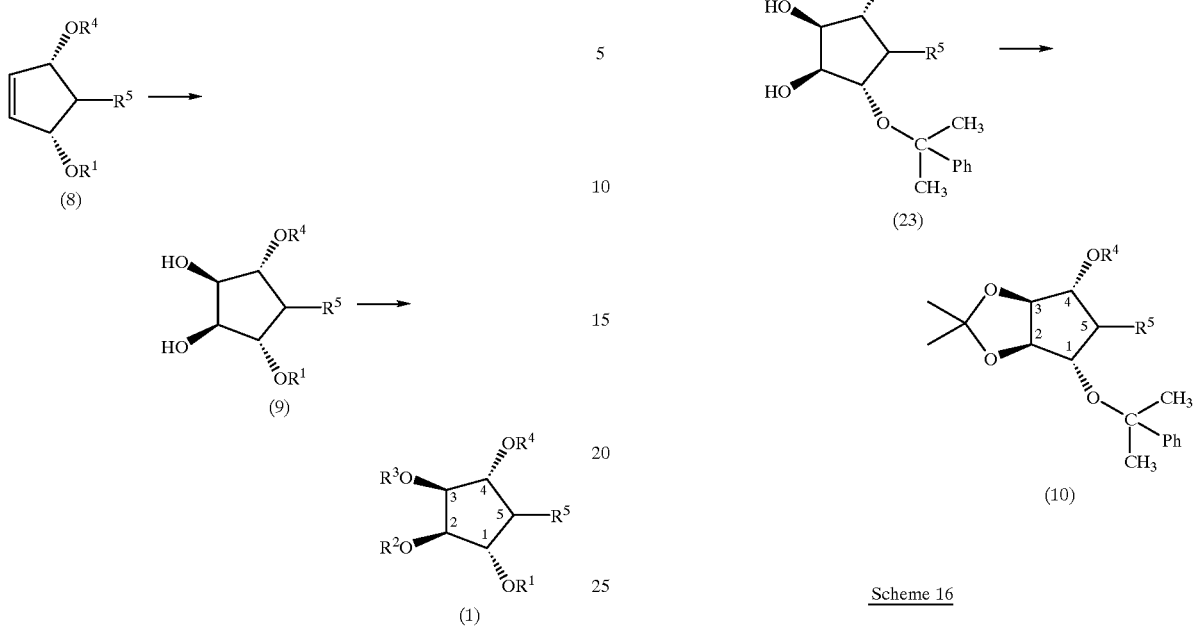

wherein $R^1$ and $R^5$ are as defined above.

Specifically, the cyclopentadiene derivatives represented by the formula (8) wherein $R^1$ is a cumyl group and $R^5$ is a hydrogen atom, i.e., (+)-cis-4-cumyloxy-2-cyclopenten-1-ol derivative, may be prepared according to the method disclosed in our report (Synlett 1999, 11, 1754–1756).

More specifically, racemic cis-4-cumyloxy-2-cyclopenten-1-ol is first prepared from dicyclopentadiene. Then, the racemate is transesterified or esterified by treating with a carboxylic acid ester or a carboxylic acid in the presence of a hydrolase to prepare (+)-cis-4-cumyloxy-2-cyclopenten-1-ol. Thereafter, the hydroxyl group is again protected with other protecting group $R^4$ than a cumyl group to prepare (+)-cis-4-cumyloxy-2-cyclopenten-1-ol derivative represented by the formula (22).

The compound (22) thus prepared is then subjected to osmium oxidation to form the diol compound (23) and then the hydroxyl groups are protected with acetonide to prepare the compound (10).

The Steps A, B and C are illustrated below.

1) Step A

The step A is the step wherein the protecting group at the 1-position of the optically active compound (1) is deprotected to prepare the optically active compound (2). Any well-known deprotection reaction may be applied provided that only the protecting group at the 1-position can be deprotected without deprotecting the protecting group at the 4-position. A preferable deprotection reaction may depend on combination of the 1-protecting group with the 4-protecting group. For instance, a catalytic reduction reaction using a palladium-carbon catalyst under hydrogen atmosphere is preferable when the protecting group at the 1-position is a cumyl group and the protecting group at the 4-position is a t-butyldimethylsilyl group.

Those skilled in the art could easily select the optimum protecting group in accordance with, for example, Theodora W. Green, Peter G. M. Wuts, "Protecting groups in Organic Synthesis", Third Ed., Wiley-Interscience. Also, it will be easy for those skilled in the art to optimize reaction conditions, for example, solvents or reaction temperatures.

The compound represented by the formula (2) prepared in the step A, may be isolated by any well-known isolation method. The compound may be isolated and purified, for example, by extraction or liquid chromatography. The isolated compound (2) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify the compound (2) as prepared in the step A and then identify the isolated compound according to any well-known method.

The compound (2) as prepared and isolated according to the process of the invention has a high purity and a high optical purity.

2) Step B

The step B is the step wherein the hydroxyl group in the optically active compound (2) as prepared in the step A is oxidized to a ketone group to prepare the optically active compound (3). Any well-known oxidation reaction may be applied provided that it may oxidize the hydroxyl group of the compound (2) to a ketone group. Preferably, the oxidation reaction is carried out without damaging the protecting groups $R^2$, $R^3$ and $R^4$.

The oxidizing agent used in the step for oxidizing the hydroxyl group in the compound (2) to a ketone group to prepare the compound (3) is not restricted provided that it can oxidize only the hydroxyl group without damaging the protecting groups $R^2$, $R^3$ and $R^4$. Preferable are heavy metal-type oxidizing agents or organic compound-type oxidizing agents. Heavy metal-type oxidizing agents may include, for example, potassium permanganate, manganese dioxide, chromium oxide-pyridine complex, pyridinium chlorochromate, pyridinium dichromate, lead acetate or silver carbonate. Organic compound-type oxidizing agents may include, for example, m-chloroperbenzoic acid, dimethyl sulfoxide/oxalyl chloride or Dess-Martin reagent.

Organic compound-type oxidizing agents are particularly preferable, with Dess-Martin reagent being more preferable.

The compound represented by the formula (3) prepared in the step B may be isolated by any well-known isolation method, for example, by extraction or liquid chromatography. The isolated compound (3) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify, and identify the compound (3) according to any known methods.

The compound (3) prepared and isolated according to the present process has a high purity and a high optical purity.

3) Step C

The step C is the step wherein the protecting group at the 4-position of the compound (3) as prepared in the step B is deprotected to form a double bond between the carbon atom at the 4-position and the carbon atom at the 5-position, whereby the optically active compound (4) is prepared. Any well-known reaction may be applied provided that it may deprotect the protecting group $R^4$ at the 4-position of the compound (3) to form a double bond between the carbon atom at the 1-position and the carbon atom at the 4-position. Preferably, the reaction is one wherein $R^4$ is deprotected without any damage to the protecting groups $R^2$ and $R^3$ to form a double bond between the carbon atom at the 4-position and the carbon atom at the 5-position. For instance, when the protecting groups $R^2$ and $R^3$ form acetonide and the protecting group $R^4$ at the 4-position is a t-butyldimethylsilyl group, it is preferable that the t-butyldimethylsilyl group is deprotected by a reaction in acetic acid at 60° C. and a double bond is formed between the carbon atoms at the 4-position and the 5-position by dehydration reaction.

Those skilled in the art may easily select the optimum reaction from well-known reactions.

The compound represented by the formula (4) prepared in the step C may be isolated by any well-known isolation method, for example, by extraction or liquid chromatography. The isolated compound (4) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify, and identify the compound (4) according to any known methods.

When the compound represented by the formula (4) is a known compound, the compound may also be identified by comparing the measurements obtained with those as referred to in literatures.

The compound (4) prepared and isolated according to the present process has a high purity and a high optical purity.

According to the lower route in the aforementioned Scheme 7, the optically active enone represented by the formula (7) may be prepared starting from the compound represented by the formula (1) through the step A', the step B' and the step C'. Each of these steps will be explained below.

1) Step A'

The step A' is the step wherein the protecting group at the 4-position of the optically active compound (1) is deprotected to prepare the optically active compound (5). Any well-known deprotection reaction may be applied provided that only the protecting group at the 4-position can be deprotected without deprotecting the protecting group at the 1-position. A preferable deprotection reaction may depend on combination of the 1-protecting group with the 4-protecting group. For instance, the deprotection reaction using tetrabutylammonium fluoride in a solvent is preferable, when the protecting group at the 1-position $R^1$ is a cumyl group and the protecting group at the 4-position $R^4$ is a t-butyldimethylsilyl group.

The compound represented by the formula (5) prepared in the step A' may be isolated by any well-known isolation method. The compound may be isolated and purified, for example, by extraction or liquid chromatography. The isolated compound (5) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify the compound (5) as prepared in the step A' and then identify the isolated compound according to any well-known method.

The compound (5) as prepared and isolated according to the process of the invention has a high purity and a high optical purity.

2) Step B'

The step B' is the step wherein the hydroxyl group in the optically active compound (5) as prepared in the step A' is oxidized to a ketone group to prepare the optically active compound (6). Any well-known oxidation reaction may be applied provided that it may oxidize the hydroxyl group of the compound (5) to a ketone group. Preferably, the oxidation reaction is carried out without damaging the protecting groups $R^1$, $R^2$ and $R^3$.

The oxidizing agent used in the step for oxidizing the hydroxyl group in the compound (5) to a ketone group to prepare the compound (6) is not restricted provided that it can oxidize only the hydroxyl group without damaging the protecting groups $R^1$, $R^2$ and $R^3$. Preferable are heavy metal-type oxidizing agents or organic compound-type oxidizing agents. Heavy metal-type oxidizing agents may include, for example, potassium permanganate, manganese dioxide, chromium oxide-pyridine complex, pyridinium chlorochromate, pyridinium dichromate, lead acetate or silver carbonate. Organic compound-type oxidizing agents may include, for example, m-chloroperbenzoic acid, dimethyl sulfoxide/oxalyl chloride or Dess-Martin reagent. Organic compound-type oxidizing agents are particularly preferable, with Dess-Martin reagent being more preferable.

The compound represented by the formula (6) prepared in the step B' may be isolated by any well-known isolation method, for example, by extraction or liquid chromatography. The isolated compound (6) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify, and identify the compound (6) according to any known methods.

The compound (6) prepared and isolated according to the present process has a high purity and a high optical purity.

3) Step C'

The step C' is the step wherein the protecting group at the 1-position of the compound (6) as prepared in the step B' is deprotected to form a double bond between the carbon atom at the 1-position and the carbon atom at the 5-position, whereby the optically active compound (7) is prepared. Any well-known reaction may be applied provided that it may deprotect the protecting group $R^1$ at the 1-position of the compound (6) to form a double bond between the carbon atom at the 1-position and the carbon atom at the 5-position. Preferably, the reaction is one wherein $R^1$ is deprotected without any damage to the protecting groups $R^2$ and $R^3$ to form a double bond between the carbon atom at the 1-position and the carbon atom at the 5-position. For instance, when the protecting groups $R^2$ and $R^3$ form acetonide and the protecting group $R^1$ at the 1-position is a cumyl group, it is preferable that the cumyl group is deprotected by a reaction in acetic acid at 60° C. and a double bond is formed between the carbon atoms at the 1-position and the 5-position by dehydration reaction.

Those skilled in the art may easily select the optimum reaction from well-known reactions.

The compound represented by the formula (7) prepared in the step C' may be isolated by any well-known isolation method, for example, by extraction or liquid chromatography. The isolated compound (7) may be identified by any well-known analytical method. The molecular structure thereof may be determined, for example, by determining spectra such as mass spectra, infrared absorption spectra or nuclear magnetic resonance spectra as well as elementary analysis. Those skilled in the art may easily isolate and purify, and identify the compound (7) according to any known methods.

When the compound represented by the formula (7) is a known compound, the compound may also be identified by comparing the measurements obtained with those as referred to in literatures.

The compound (7) prepared and isolated according to the present process has a high purity and a high optical purity.

The invention will be illustrated in greater detail by way of the following Examples, but the invention is not to be limited thereto. And, the reactions for the optically active enones as obtained by the following examples are as shown in the following Schemes 17–22.

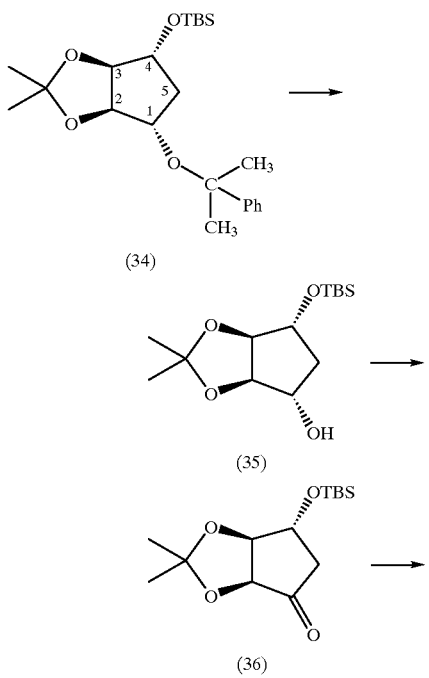

Scheme 17

(34)

(35)

(36)

-continued
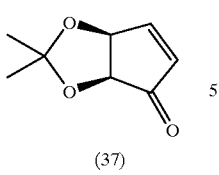
(37)
Scheme 18
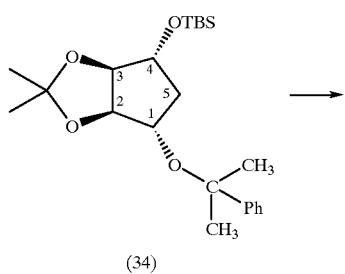
(34)
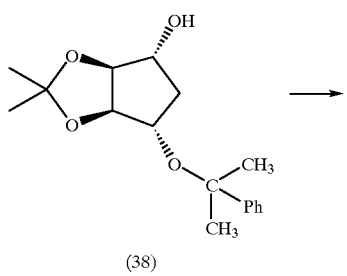
(38)
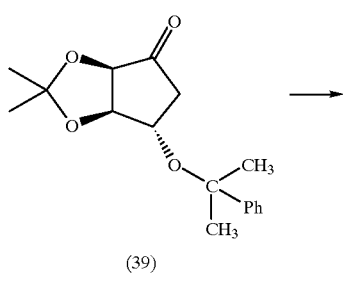
(39)
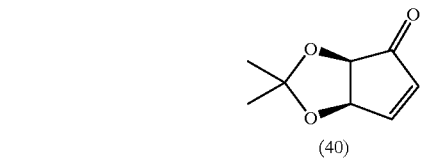
(40)
Scheme 19
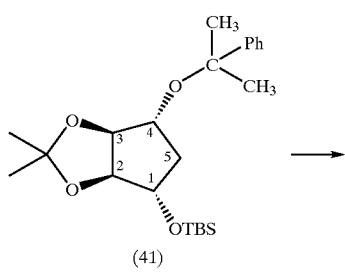
(41)
-continued
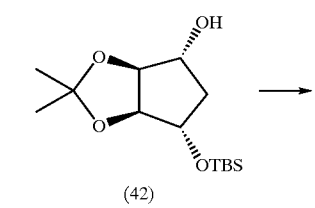
(42)
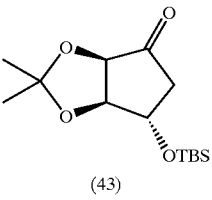
(43)
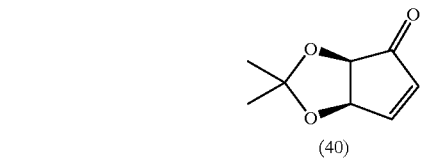
(40)
Scheme 20
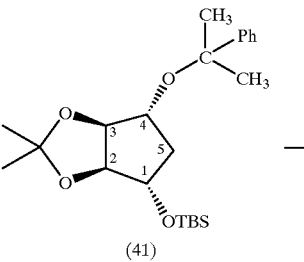
(41)
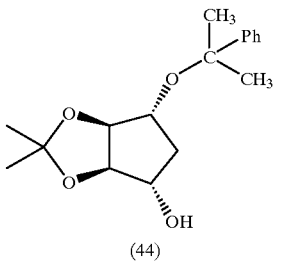
(44)
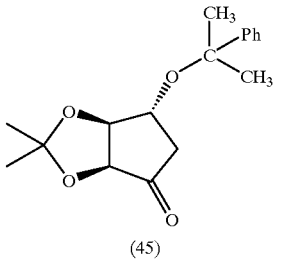
(45)
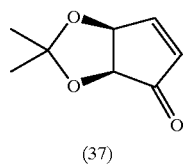
(37)

Scheme 21

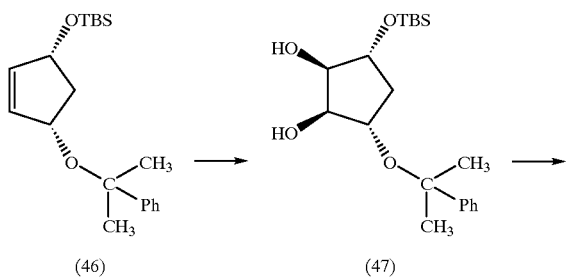

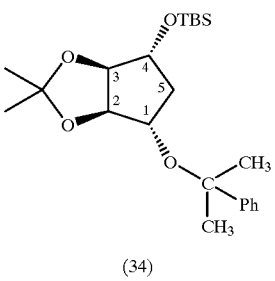

Scheme 22

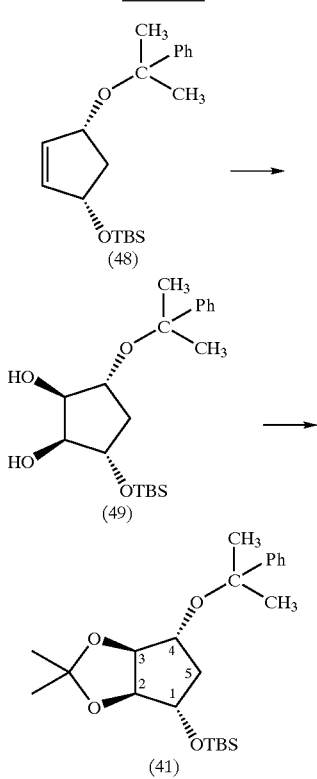

EXAMPLE 1

Preparation of the optically active compound of the formula (47): (Case 1)

In 40 ml of dimethylformamide (DMF) were dissolved 4.02 g of (+)-cis-4-cumyloxy-2-cyclopenten-1-ol and 2.04 g of imidazole and the solution was stirred at room temperature. A DMF solution of 3.2 g of t-butyldimethylsilyl chloride was added dropwise thereto. After completion of the dropwise addition, the reaction solution was stirred at room temperature for 3 hours and then poured into water. It was extracted twice with ethyl acetate. The organic layer was washed with a saturated aqueous solution of sodium chloride and then dried over anhydrous magnesium sulfate. After the drying agent was filtered off, the filtrate was concentrated under reduced pressure, and the residue was purified on silica gel column (acetone/hexane=1/8) to afford 6.07 g of the compound of the formula (46). Yield was 99%.

Subsequently, 3.82 g (11.5 mmol) of the compound (46) was dissolved in a mixed solvent of 20 ml of tetrahydrofuran (THF) and 20 ml of water and to the solution were added 2.5 ml. of osmium tetroxide and 2.02 g of N-methylmorpholine-N-oxide (NMO). The mixture was stirred at room temperature for 18 hours. After completion of the reaction, the reaction mixture was saturated with sodium sulfite and extracted with ethyl acetate. The organic layer was washed with a dilute aqueous solution of sodium hydroxide and a saturated aqueous solution of sodium chloride and then dried over anhydrous magnesium sulfate. After the drying agent was filtered off and the solvent distilled off, the residue was purified on silica gel column (acetone/hexane=1/4). The resulting solid was recrystallized from hexane to afford 3.83 g (10.5 mmol) of the compound (47), having a melting point of 48–49° C. Yield was 91%.

Measurements of physical properties for the compound (47) are shown below:

$[\alpha]_D^{31}$ +12.62° (c 0.99, chloroform)
$^1$H-NMR (CDCl$_3$): δ=0.034 (s, 3H), 0.042 (s, 3H), 0.881 (s, 9H), 1.48 (ddd, 1H, J=13.5, 7.2, 7.2 Hz), 1.54 (s, 3H), 1.58 (s, 3H), 2.19 (ddd, 1H, J=13.5, 8.0, 6.7 Hz), 2.29 (bs, 1H), 2.50 (bs, 1H), 3.55 (ddd, 1H, J=8.0, 7.2, 4.7 Hz), 3.80 (dd, 1H, J=4.7, 4.7 Hz), 3.83 (ddd, 1H, J=7.2, 6.7, 4.7 Hz), 3.98 (dd, 1H, J=4.7, 4.7 Hz), 7.23–7.48 (m, 5H)

EXAMPLE 2

Preparation of the optically active compound of the formula (47): (Case 2)

In a mixed solvent of 75 ml of tetrahydrofuran (THF) and 75 ml of water was dissolved 11.25 g (33.83 mmol) of the compound (46), and 4.3 ml (0.85 mmol) of a 0.196M THF solution of osmium tetroxide and 5.95 g (50.8 mmol) of N-methylmorpholine-N-oxide (NMO) were added. The resulting mixture was stirred at room temperature for 3 days. After completion of the reaction, 5 ml of a saturated aqueous solution of sodium sulfite was added and the mixture was extracted three times with 200 ml of ethyl acetate. The organic layer was washed with 50 ml of a saturated aqueous solution of sodium chloride and dried over anhydrous magnesium sulfate. After the solvent was distilled off under reduced pressure, the residue was purified on a silica gel column (500 g of silica gel, ethyl acetate/hexane 1/4 v/v). The resulting solid was recrystallized from hexane to give 11.16 g of the compound (47) with a melting point of 48–49° C. as colorless needles. Yield was 90%.

Measurements of physical properties for the compound (47) are shown below:

$[\alpha]_D^{30}$ +10.16° (c 0.734, chloroform)
IR (film): ν=1764 cm$^{-1}$
$^1$H-NMR (CDCl$_3$): δ=0.034 (s, 3H), 0.042 (s, 3H), 0.881 (s, 9H), 1.48 (ddd, 1H, J=13.5, 7.2, 7.2 Hz), 1.54 (s, 3H), 1.58 (s, 3H), 2.19 (ddd, 1H, J=13.5, 8.0, 6.7 Hz), 2.29 (bs, 1H), 2.50 (bs, 1H), 3.55 (ddd, 1H, J=8.0, 7.2, 4.7 Hz), 3.80 (dd, 1H, J=4.7, 4.7 Hz), 3.83 (ddd, 1H, J=7.2, 6.7, 4.7 Hz), 3.98 (dd, 1H, J=4.7, 4.7 Hz), 7.23–7.48 (m, 5H)
$^{13}$C-NMR (CDCl$_3$): δ=−4.89, 17.90, 25.65, 28.71, 28.78, 39.24, 74.89, 76.:33, 76.89, 77.38, 77.50, 126.08, 127.21, 128.27, 146.85
MS: m/z=351 (M$^+$-CH$_3$), 309 (M$^+$-t-C$_4$H$_9$), 229 (M$^+$-C$_9$H$_{13}$O)

HRMS: m/z Calc'd $C_{11}H_{21}O_3Si$ ($M^+-C_4H_9O$): 229.1260, Found 229.1278

Elemental analysis: Calc'd for $C_{20}H_{34}O_4Si$ (366.6): C 65.53, H 9.35, Found: C 65.64, H 9.35

EXAMPLE 3

Following the same procedure as described in Example 2, the compound (49), which is the enantiomer of the compound (47), was prepared from the compound (48), which is the enantiomer of the compound (46). Yield was 90%.

Measurements of physical propertied for the compound (49) are shown below:

Melting point 48–49° C.

$[\alpha]_D^{30}$ –10.25° (c 0.752, chloroform)

EXAMPLE 4

Preparation of the optically active compound of the formula (34): (Case 1)

In 30 ml of dichloromethane was dissolved 3.69 g (10.1 mmol) of the compound (47) obtained in Example 1. 12.4 ml of acetone dimethyl ketal and 25 mg of p-toluenesulfonic acid were added, and the mixture was stirred at room temperature for 15 hours. To the reaction solution was added a saturated aqueous solution of sodium bicarbonate and the mixture was extracted with ether. The organic layer was washed with a dilute aqueous solution of sodium hydroxide and a saturated aqueous solution of sodium chloride and then dried over anhydrous magnesium sulfate. After the drying agent was filtered off and the solvent distilled off, the residue was purified on silica gel column (acetone/hexane=1/16) to afford 2.90 g (7.14 mmol) of the compound (34) as a colorless oily substance. Yield was 71%.

Measurements of physical properties for the compound (34) are shown below:

$[\alpha]_D^{32}$ –20.76° (c 1.00, chloroform)

$^1$H-NMR (CDCl$_3$): δ=0.060 (s, 3H), 0.071 (s, 3H), 0.897 (s, 9H), 1.24 (s, 3H), 1.33 (s, 3H), 1.50 (s, 3H), 1.61 (s, 3H), 1.71 (ddd, 1H, J=13.5, 6.6, 6.6 Hz), 2.07 (ddd, 1H, J=13.5, 6.6, 6.6 Hz), 3.66 (ddd, 1H, J=6.5, 6.5, 2.0 Hz), 3.98 (ddd, 1H, J=6.9, 6.5, 2.7 Hz), 4.37 (dd, 1H, J=6.9, 2.7 Hz), 4.51 (dd, 1H, J=6.9, 2.0 Hz), 7.21–7.47 (m, 5H)

EXAMPLE 5

Preparation of the optically active compound of the formula (34): (Case 2)

In 115 ml of dichloromethane was dissolved 11.16 g (30.44 mmol) of the compound (47) obtained in Example 2. 37 ml (300 mmol) of acetone dimethyl ketal and 76 mg (0.3 mmol) of p-toluenesulfonic acid were added, and the mixture was stirred at room temperature for 24 hours. To the reaction solution was added 100 ml of a saturated aqueous solution of sodium bicarbonate and the mixture was extracted twice with 150 ml of diethyl ether. The organic layer was dried over anhydrous magnesium sulfate and the solvent was distilled off under reduced pressure. The residue was purified on silica gel column (500 g of silica gel, ethyl acetate/hexane =1/20 v/v) to afford 12.04 g of the compound (34) as a colorless oily substance. Yield was 97%.

Measurements of physical properties for the compound (34) are shown below:

$[\alpha]_D^{32}$ –20.76° (c 1.01, chloroform)

$^1$H-NMR (CDCl$_3$): δ=0.060 (s, 3H), 0.071 (s, 3H), 0.897 (s, 3H), 1.24 (s, 3H), 1.33 (s, 3H), 1.50 (s, 3H), 1.61 (s, 3H), 1.71 (ddd, 1H, J=13.5, 6.6, 6.6 Hz), 2.07 (ddd, 1H, J=13.5, 6.6, 6.6 Hz), 3.66 (ddd, 1H, J=6.5, 6.5, 2.9 Hz), 3.98 (ddd, 1H, J=6.5, 6.5, 2.7 Hz), 4.37 (dd, 1H, J=6.9, 2.7 Hz), 4.51 (dd, 1H, J=6.9, 2.0 Hz), 7.21–7.47 (m, 5H)

$^{13}$C-NMR (CDCl$_3$): δ=–4.88, 17.91, 24.55, 25.70, 26.73, 27.32, 30.42, 40.52, 76.62, 77.14, 77.67, 86.49, 86.78, 110.87, 126.08, 126.86, 128.09, 147.16

MS: m/z=391 ($M^+$-CH$_3$), 287 ($M^+$-C$_9$H$_{11}$)

HRMS: m/z Calc'd $C_{14}H_{27}O_4Si$ ($M^+$-C$_9$H$_{11}$): 287.1679, Found 287.1678

Elemental analysis: Calc'd for $C_{23}H_{38}O_4Si$ (406.6): C 67.94, H 9.42, Found: C 67.85, H 9.51

EXAMPLE 6

Following the same procedure as described in Example 5, the compound (41), which is the enantiomer of the compound (34), was prepared from the compound (49), which is the enantiomer of the compound (47). Yield was 97%.

Measurements of physical properties for the compound (41) are shown below:

$[\alpha]_D^{+}$20.76° (c 0.95, chloroform)

EXAMPLE 7

Preparation of the optically active compound of the formula (35): (Case 1)

In 18 mL of ethyl acetate was dissolved 1.45 g (3.57 mmol) of the compound (34) obtained in Example 4. 107 mg of 10% palladium-carbon and two drops of chloroform were added and then catalytic reduction was carried out at room temperature. After completion of the reaction, the catalyst was filtered off and the filtrate was concentrated under reduced pressure. The residue was purified on silica gel column (acetone/hexane=1/8) to afford 982 mg (3.40 mmol) of the compound (35) as a colorless oily substance. Yield was 95%.

Measurements of physical properties for the compound (35) are shown below:

$[\alpha]_D^{30}$ –4.62° (c 1.06, chloroform)

$^1$H-NMR (CDCl$_3$): δ=0.124 (s, 3H), 0.134 (s, 3H), 0.892 (s, 9H), 1.29 (s, 3H), 1.39 (s, 3H), 1.76 (d, 1H, J=14.4 Hz), 2.09 (ddd, 1H, J=14.4, 4.2, 4.2 Hz), 3.21 (d, 1H, J=11.3 Hz), 4.09 (dd, 1H, J=11.3, 4.2 Hz), 4.25 (d, 1H, J=4.2 Hz), 4.51 (dd, 1H, J=5.7, 1.5 Hz), 4.66 (dd, 1H, J=5.7, 1.5 Hz)

EXAMPLE 8

Preparation of the optically active compound of the formula (35): (Case 2)

In 100 ml of ethyl acetate was dissolved 10.00 g (24.62 mmol) of the compound (34) obtained in Example 5. 756 mg of 10% palladium-carbon and three drops of chloroform were added and then catalytic reduction was carried out under hydrogen atmosphere at room temperature for 17 hours. After completion of the reaction, the catalyst was filtered off and the filtrate was concentrated under reduced pressure. The residue was purified on silica gel column (500 g of silica gel, ethyl acetate/hexane=1/8 v/v) to afford 982 mg (3.40 mmol) of the compound (35) as a colorless oily substance. Yield was 95%.

Measurements of physical properties for the compound (35) are shown below:

$[\alpha]_D^{28}$ –5.42° (c 1.11, chloroform)

$^1$H-NMR (CDCl$_3$): δ=0.124 (s, 3H), 0.134 (s, 3H), 0.892 (s, 9H), 1.29 (s, 3H), 1.39 (s, 3H), 1.76 (d, 1H, J=14.4 Hz), 2.09 (ddd, 1H, J=14.4, 4.2, 4.2 Hz), 3.21 (d, 1H, J=11.3 Hz), 4.09 (dd, 1H, J=11.3, 4.2 Hz), 4.25 (d, 1H, J=4.2 Hz), 4.51 (dd, 1H, J=5.7, 1.5 Hz), 4.66 (dd, 1H, J=5.7, 1.5 Hz)

$^{13}$C-NMR (CDCl$_3$): δ=–5.27, –5.15, 17.74, 23.68, 25.58, 26.02, 37.24, 77.53, 78.40, 85.82, 86.43, 110.10

MS: m/z=289 ($M^+$+H), 273 ($M^+$-CH$_3$)

HRMS: m/z Calc'd $C_{13}H_{25}O_4Si$ ($M^+$-CH$_3$): 273.1522, Found 273.1524

Elemental analysis: Calc'd for $C_{14}H_{28}O_4Si$ (288.5): C 58.29, H 9.78, Found: C 58.31, H 9.60

EXAMPLE 9

Following the same procedure as described in Example 8, the compound (42), which is the enantiomer of the compound (35), was prepared from the compound (41), which is the enantiomer of the compound (34). Yield was 96%.

Measurements of physical properties for the compound (42) are shown below:

$[\alpha]_D^{25}$+5.52° (c 1.02, chloroform)

EXAMPLE 10

Preparation of the optically active compound of the formula (36): (Case 1)

In 15 mL of dichloromethane was dissolved 753 mg (2.61 mmol) of the compound (35) obtained in Example 7 and the solution was stirred at room temperature. To the solution was added 1.64 g of Dess-Martin reagent and the mixture was stirred for 10 minutes. After completion of the reaction, a 5% sodium hydroxide solution was added and the mixture was extracted with ethyl acetate. The organic layer was washed with a dilute sodium hydroxide solution and a saturated aqueous solution of sodium chloride and then dried over anhydrous magnesium sulfate. After the drying agent was filtered off and the solvent was distilled off, the residue was purified on silica gel column (acetone/hexane=1/2) to afford 720 mg (2.51 mmol) of the compound (36) as a colorless oily substance. Yield was 96%.

Measurements of physical properties for the compound (36) are shown below:

$[\alpha]_D^{31}$+133.48° (c 1.16, chloroform)

$^1$H-NMR (CDCl$_3$): δ=0.085 (s, 3H), 0.11 (s, 3H), 0.87 (s, 9H), 1.35 (s, 3H), 1.42 (s, 3H), 2.17 (d, 1H, J=18 Hz), 2.82 (dd, 1H, J=18, 5.0 Hz), 4.30 (d, 1H, J=5.4 Hz), 4.42 (d, 1H, J=5.0 Hz), 4.54 (d, 1H, J=5.4 Hz)

EXAMPLE 11

Preparation of the optically active compound of the formula (36): (Case 2)

In 100 ml of dichloromethane was dissolved 6.14 g (21.29 mmol) of the compound (35) obtained in Example 8 and the solution was stirred at room temperature. To the solution was added 14.60 g (35.00 mmol) of Dess-Martin reagent and the mixture was stirred for 30 minutes. After completion of the reaction, 100 ml of a 0.5N sodium hydroxide solution was added and the mixture was extracted twice with 100 ml of ethyl acetate. The organic layer was washed with 20 ml of a saturated aqueous solution of sodium chloride and dried over anhydrous magnesium sulfate. After the drying agent was filtered off and the solvent was distilled off under reduced pressure, the residue was purified on silica gel column (420 g of silica gel, ethyl acetate/hexane=1/8 v/v) to afford 5.94 g of the compound (36) as a colorless oily substance. Yield was 97%.

Measurements of physical properties for the compound (36) are shown below:

$[\alpha]_D^{31}$+133.48° (c 1.16, chloroform)

IR (film): ν=1764 cm$^{-1}$ $^1$H-NMR (CDCl$_3$): δ=0.085 (s, 3H), 0.11 (s, 3H), 0.87 (s, 9H), 1.35 (s, 3H), 1.42 (s, 3H), 2.17 (d, 1H, J=18.0 Hz), 2.82 (dd, 1H, J=18.0, 5.0 Hz), 4.30 (d, 1H, J=5.4 Hz), 4.42 (d, 1H, J=5.0 Hz), 4.54 (d, 1H, J=5.4 Hz)

$^{13}$C-NMR (CDCl$_3$): δ=−5.11, 17.79, 24.68, 25.49, 26.63, 43.07, 69.18, 77.99, 82.75, 112.80, 212.24

MS: m/z=271 (M$^+$-CH$_3$)

HRMS: m/z Calc'd $C_{13}H_{23}O_4Si$ (M$^+$-CH$_3$): 271.1366, Found 271.1350

Elemental analysis: Calc'd for $C_{14}H_{26}O_4Si$ (286.5): C 58.76, H 9.15, Found: C 58.76, H 9.30

EXAMPLE 12

Following the same procedure as described in Example 11, the compound (43), which is the enantiomer of the compound (36), was prepared from the compound (42), which is the enantiomer of the compound (35). Yield was 97%.

Measurements of physical properties for the compound (43) are shown below:

Melting point 110–111° C.

$[\alpha]_D^{28}$−136.59° (c 1.22, chloroform)

EXAMPLE 13

Preparation of (+)-7,7-dimethyl-6,8-dioxabicyclo[3,3,0]oct-3-en-2-one of the formula (37): (Case 1)

In 8.3 ml of acetic acid was dissolved 720 mg (2.51 mmol) of the compound (36) obtained in Example 10, and the solution was stirred at 60° C. for 3 days and then at 90° C. for one day. The reaction solution was added to an excess of a dilute aqueous solution of sodium hydroxide, and the mixture was extracted with ether. The organic layer was washed with a dilute sodium hydroxide solution and a saturated aqueous solution of sodium chloride and then dried over anhydrous magnesium sulfate. After the drying agent was filtered off and the solvent was distilled off, the residue was purified on silica gel column (acetone/hexane=1/2) to afford 269 mg (1.74 mmol) of (+)-7,7-dimethyl-6,8-dioxabicyclo[3,3,0]oct-3-en-2-one (37). Yield was 69%.

Measurements of physical properties for the (+) enone form (37) are as shown below and these data are in consistency with those in literatures:

$[\alpha]_D^{32}$−69.88° (c 0.99, chloroform)

$^1$H-NMR (CDCl$_3$): δ=1.35 (s, 6H), 4.40 (d, 1H, J=5.4 Hz), 5.21 (dd, 1H, J=2.1, 5.4 Hz), 6.15 (d, 1H, J=5.7 Hz), 7.55 (dd, 1H, J=2.1, 5.7 Hz)

EXAMPLE 14

Preparation of (+)-7,7-dimethyl-6,8-dioxabicyclo[3,3,0]oct-3-en-2-one of the formula (37): (Case 2)

In 100 ml of acetic acid was dissolved 5.17 g (18.05 mmol) of the compound (36) obtained in Example 11 and the solution was stirred at 60° C. for 4 days. After cooling, the reaction solution was diluted with 300 ml of diethyl ether and washed successively with 100 ml of a saturated aqueous solution of sodium chloride and 100 ml of a 1N aqueous solution of sodium hydroxide. The organic layer was dried over anhydrous magnesium sulfate and then the solvent was distilled off under reduced pressure. The residue was purified on silica gel column (250 g of silica gel, diethyl ether/hexane=1/3–1/1 v/v) to afford 2.18 g of (+)-7,7-dimethyl-6,8-dioxabicyclo[3,3,0]oct-3-en-2-one (37). Yield was 78%.

Measurements of physical properties for the (+) enone form (37) are as shown below and these data are in consistency with those in literatures (Melting point 68–69° C., $[\alpha]_D^{25}$+70.49° (c 0.95, chloroform)).

Melting point 68–69° C.

$[\alpha]_D^{32}$+69.70° (c 1.18, chloroform)

EXAMPLE 15

Following the same procedure as described in Example 14, the compound (40), which is the enantiomer of the compound (37), was prepared from the compound (43), which is the enantiomer of the compound (36). Yield was 78%.

Measurements of physical properties for the compound (40) are shown below:

Melting point 68–69° C.

$[\alpha]_D^-$ −69.33° (c 1.22, chloroform)

EXAMPLE 16

Preparation of the optically active compound of the formula (38): (Case 1)

In 10 ml of THF was dissolved 1.41 g (3.47 mmol) of the compound (34) obtained in Example 4 and the solution was stirred at 0° C. To the solution was added 4.5 ml of tetrabutylammonium fluoride (TBAF), and the mixture was allowed to rise up to room temperature and then stirred for one hour. The reaction solution was poured into water and extracted with ethyl acetate. The organic layer was washed with a dilute sodium hydroxide solution and a saturated aqueous solution of sodium chloride and then dried over anhydrous magnesium sulfate. After the drying agent was filtered off and the solvent was distilled off, the residue was purified on silica gel column (acetone/hexane=1/4). The resulting solid was recrystallized from ethyl acetate/hexane to afford 952 mg (3.26 mmol) of the compound (38). Yield was 94%.

Measurements of physical properties for the compound (38) are shown below:

Melting point 110–111° C.

$[\alpha]_D^{31}$ −19.53° (c 1.08, chloroform)

$^1$H-NMR (CDCl$_3$): δ=1.25 (s, 3H), 1.31 (s, 3H), 1.56 (s, 3H), 1.63 (s, 3H), 1.74 (d, 1H, J=14.4 Hz), 1.96 (ddd, 1H, J=14.4, 4.5, 4.5 Hz), 3.33 (d, 1H, J=11.0 Hz), 3.87 (d, 1H, J=4.5 Hz), 4.05 (dd, 1H, J=11.0, 4.5 Hz), 4.60 (dd, 1H, J=5.7, 1.5 Hz), 4.61 (dd, 1H, J=5.7, 1.5 Hz), 7.25–7.45 (m, 5H)

EXAMPLE 17

Preparation of the optically active compound of the formula (38): (Case 2)

In 50 ml of THF was dissolved 9.18 g (22.58 mmol) of the compound (34) obtained in Example 5 and the solution was stirred at 0° C. To the solution was added 27 ml (27 mmol) of a 1.0M THF solution of tetrabutylammonium fluoride (TBAF), and the mixture was allowed to rise up to room temperature and then stirred for two and half hours. The reaction solution was extracted twice with 100 ml of ethyl acetate. The organic layer was washed with 20 ml of a saturated aqueous solution of sodium chloride and dried over anhydrous magnesium sulfate. After the solvent was distilled off under reduced pressure, the residue was purified on silica gel column (450 g of silica gel, ethyl acetate/hexane=1/4 v/v). The resulting solid was recrystallized from ethyl acetate/hexane to afford 6.17 g of the compound (38). Yield was 93%.

Measurements of physical properties for the compound (38) are shown below:

Melting point 110–111° C.

$[\alpha]_D^{31}$ −19.53° (c 1.08, chloroform)

IR (film): ν=3500 cm$^{-1}$ $^1$H-NMR (CDCl$_3$): δ=1.25 (s, 3H), 1.31 (s, 3H), 1.56 (s, 3H), 1.63 (s, 3H), 1.74 (d, 1H, J=14.4 Hz), 1.96 (ddd, 1H, J=14.4, 4.5, 4.5 Hz), 3.33 (d, 1H, J=11.0 Hz), 3.87 (d, 1H, J=4.5 Hz), 4.05 (dd, 1H, J=11.0, 4.5 Hz), 4.60 (dd, 1H, J=5.7, 1.5 Hz), 4.61 (dd, 1H, J=5.7, 1.5 Hz), 7.25–7.45 (m, 5H)

$^{13}$C-NMR (CDCl$_3$): δ=23.67, 25.96, 27.37, 29.60, 36.45, 77.26, 78.67, 79.17, 85.32, 86.37, 109.98, 126.02, 127.50, 128.38, 145.20

MS: m/z=29:2 (M$^+$)

HRMS: m/z Calc'd C$_{17}$H$_{24}$O$_4$: 292.1675, Found 292.1695

Elemental analysis: Calc'd for C$_{17}$H$_{24}$O$_4$ (292.4): C 69.84, H 8.27, Found: C 69.89, H 8.24

EXAMPLE 18

Following the same procedure as described in Example 17, the compound (44), which is the enantiomer of the compound (38), was prepared from the compound (41), which is the enantiomer of the compound (34). Yield was 98%.

Measurements of physical properties for the compound (44) are shown below:

Melting point 110–111° C.

(Recrystallized from ethyl acetate/hexane)

$[\alpha]_D^{28}$ +19.75° (c 0.75, chloroform)

EXAMPLE 19

Preparation of the optically active compound of the formula (39): (Case 1)

The same procedure as described in Example 10 was carried out, except that 753 mg of the compound (35) was replaced by 633 mg (2.17 mmol) of the compound (38) obtained in Example 16, and that 1.36 g of the Dess-Martin reagent was used. After distilling off the solvent was modified, the resulting solid was recrystallized from hexane to afford 624 mg (2.15 mmol) of the compound (39). Yield was 99%.

Measurements of physical properties for the compound (39) are as shown below:

Melting point 98–99° C.

$[\alpha]_D^{31}$ −142.81° (c 1.13, chloroform)

$^1$H-NMR (CDCl$_3$): δ=1.30 (s, 3H), 1.34 (s, 3H), 1.55 (s, 3H), 1.62 (s, 3H), 2.23 (ddd, 1H, J=18.3, 3.0, 1.5 Hz), 2.67 (dd, 1H, J=18.3, 6.3 Hz), 3.99 (ddd, 1H, J=6.3, 1.5, 1.5 Hz), 4.36 (bd, 1H, J=5.4 Hz), 4.58 (d, 1H, J=5.4 Hz), 7.25–7.44 (m, 5H)

EXAMPLE 20

Preparation of the optically active compound of the formula (39): (Case 2)

In 50 ml of dichloromethane was dissolved 2.98 g (10.19 mmol) of the compound (38) and the solution was stirred at room temperature. To the solution was added 6.39 g (15.29 mmol) of Dess-Martin reagent and the mixture was stirred for 30 minutes. After completion of the reaction, 50 ml of a 0.5N sodium hydroxide solution was added and the mixture was extracted three times with 50 ml of ethyl acetate. The organic layer was washed with 10 ml of a saturated aqueous solution of sodium chloride and dried over anhydrous magnesium sulfate. After the drying agent was filtered off and the solvent was distilled off under reduced pressure, the residue was purified on silica gel column (150 g of silica gel, ethyl acetate/hexane=1/4 v/v) to afford 2.85 g of the compound (39) as colorless needles. Yield was 96%.

Measurements of physical properties for the compound (39) are shown below:

Melting point 98–99° C.

$[\alpha]_D^{31}$ −142.81° (c 1.13, chloroform)

IR (film): ν=1758 cm$^{-1}$ $^1$H-NMR (CDCl$_3$): δ=1.30 (s, 3H), 1.34 (s, 3H), 1.55 (s, 3H), 1.62 (s, 3H), 2.23 (ddd, 1H, J=18.3, 3.0, 1.5 Hz), 2.67 (dd, 1H, J=18.3, 6.3 Hz), 3.99 (ddd, 1H, J=6.3, 1.5, 1.5 Hz), 4.36 (bd, 1H, J=5.4 Hz), 4.58 (d, 1H, J=5.4 Hz), 7.25–7.44 (m, 5H)

$^{13}$C-NMR (CDCl$_3$): δ=24.76, 26.63, 27.78, 29.09, 42.63, 69.91, 78.37, 78.654, 82.51, 112.54, 125.95, 127.51, 128.39, 145.58, 212.68

MS: m/z=290 (M$^+$)

HRMS: m/z Calc'd $C_{17}H_{22}O_4$ (M+): 290.1518, Found 290.1553

Elemental analysis: Calc'd for $C_{17}H_{22}O_4$ (290.4): C 70.32, H 9.15, Found: C 70.19, H 7.58

EXAMPLE 21

Following the same procedure as described in Example 20, the compound (45), which is the enantiomer of the compound (39), was prepared from the compound (44), which is the enantiomer of the compound (38). Yield was 96%.

Measurements of physical properties for the compound (45) are shown below:

Melting point: 98–99° C.

$[\alpha]_D^{29}+144.15°$ (c 0.92, chloroform)

EXAMPLE 22

Preparation of (−)-7,7-dimethyl-6,8-dioxabicyclo[3,3,0]oct-3-en-2-one of the formula (40): (Case 1)

In 7.0 ml of acetic acid was dissolved 624 mg (2.15 mmol) of the compound (39) obtained in Example 19 and the solution was stirred at 60° C. for 3 days. The reaction solution was added to an excess of a dilute aqueous solution of sodium hydroxide, and the mixture was extracted with ether. The organic layer was washed with a dilute sodium hydroxide solution and a saturated aqueous solution of sodium chloride and then dried over anhydrous magnesium sulfate. After the drying agent was filtered off and the solvent was distilled off, the residue was purified on silica gel column (acetone/hexane=1/2) to afford 276 mg (1.79 mmol) of (−)-7,7-dimethyl-6,8-dioxabicyclo[3,3,0]oct-3-en-2-one (40). Yield was 83%.

Measurements of physical properties for the (−) enone form (40) are as shown below and these data are in consistency with those in literatures:

$[\alpha]_D^{32}+69.70°$ (c 1.18, chloroform)

$^1$H-NMR (CDCl$_3$) data are the same as those of the compound (37) obtained in Example 13.

EXAMPLE 23

Preparation of (−)-7,7-dimethyl-6,8-dioxabicyclo[3,3,0]oct-3-en-2-one of the formula (40): (Case 2)

In 50 ml of acetic acid was dissolved 2.57 g (8.85 mmol) of the compound (39) obtained in Example 20 and the solution was stirred at 60° C. for 4 days. To the reaction solution was added 150 ml of diethyl ether, and the mixture was washed successively with 50 ml of a saturated aqueous solution of sodium chloride and 50 ml of a 1N aqueous sodium hydroxide solution. The organic layer was dried over anhydrous magnesium sulfate. After the solvent was distilled off under reduced pressure, the residue was purified on silica gel column (150 g of silica gel, diethyl ether/hexane=1/1 v/v) to afford 1.03 g of (−)-7,7-dimethyl-6,8-dioxabicyclo[3,3,0]oct-3-en-2-one (40). Yield was 76%.

Measurements of physical properties for the (−) enone form (40) are as shown below and these data are in consistency with those in literatures:

Melting point 68–69° C.

$[\alpha]_D^{32}-69.88°$ (c 1.00, chloroform)

EXAMPLE 24

Following the same procedure as described in Example 23, (+)-7,7-dimethyl-6,8-dioxabicyclo[3,3,0]oct-3-en-2-one (37), which is the enantiomer of (−)-7,7-dimethyl-6,8-dioxabicyclo[3,3,0]oct-3-en-2-one (40), was prepared from the compound (45), which is the enantiomer of the compound (39). Yield was 76%.

Measurements of physical properties for the compound (37) are shown below:

Melting point 68–69° C.

$[\alpha]_D^{31}+69.36°$ (c 1.05, chloroform)

INDUSTRIAL APPLICABILITY

The process for the preparation of optically active enones according to the invention is simple and convenient. The process is highly useful, since it may be applicable to efficient synthesis of not only physiologically active substances but also general organic compounds and further it may easily be scaled up. Moreover, the intermediates obtained during the process of the preparation according to the invention, that is, the optically active compounds of the invention are similarly useful as chiral building blocks.

What is claimed is:

1. A process for the preparation of an optically active enone represented by the formula (4)

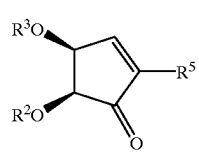

(4)

wherein $R^2$ and $R^3$ jointly represent acetonide, methyl ethyl ketal or diethyl ketal, and $R^5$ represents a hydrogen atom, an alkyl group having not more than 20 carbon atoms or a phenyl group, which comprises steps of A) deprotecting the protecting group for the hydroxyl group at the 1-position in an optically active compound represented by the formula (1)

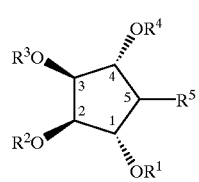

(1)

wherein $R^1$ and $R^4$ independently represent a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, and $R^2$, $R^3$ and $R^5$ are as defined above to form an optically active compound represented by the formula (2)

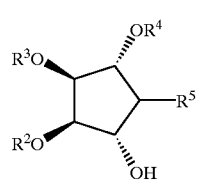

(2)

wherein $R^2$, $R^3$, $R^4$ and $R^5$ are as defined above,

B) oxidizing the hydroxyl group at the 1-position in the compound (2) to form an optically active compound represented by the formula (3)

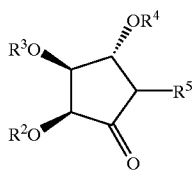

(3)

wherein $R^2$, $R^3$, $R^4$ and $R^5$ are as defined above, and

C) deprotecting the protecting group for the hydroxyl group at the 4-position in the compound (3) to form a double bond between the carbon atom at the 4-position and the carbon atom at the 5-position.

2. A process for the preparation of an optically active enone represented by the formula (7)

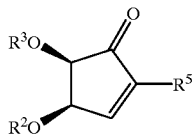

(7)

wherein $R^2$ and $R^3$ jointly represent acetonide, methyl ethyl ketal or diethyl ketal, and $R^5$ represents a hydrogen atom, an alkyl group having not more than 20 carbon atoms or a phenyl group, which comprises steps of A') deprotecting the protecting group for the hydroxyl group at the 4-position in an optically active compound represented by the formula (1)

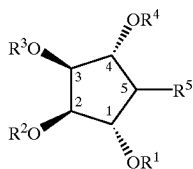

(1)

wherein $R^1$ and $R^4$ independently represent a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, and $R^2$, $R^3$ and $R^5$ are as defined above to form an optically active compound represented by the formula (5)

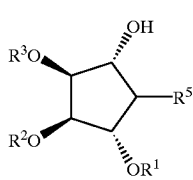

(5)

wherein $R^1$, $R^2$, $R^3$ and $R^5$ are as defined above,

B') oxidizing the hydroxyl group at the 4-position in the compound (5) to form an optically active compound represented by the formula (6)

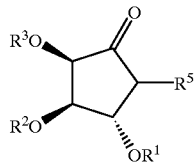

(6)

wherein $R^1$, $R^2$, $R^3$ and $R^5$ are as defined above, and

C') deprotecting the protecting group for the hydroxyl group at the 1-position in the compound (6) to form a double bond between the carbon atom at the 1-position and the carbon atom at the 5-position.

3. An optically active compound represented by the formula (1)

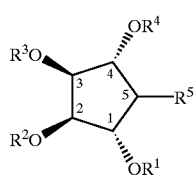

(1)

wherein $R^1$ and $R^4$ independently represent a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, $R^2$ and $R^3$ jointly represent acetonide, methyl ethyl ketal or diethyl ketal, and $R^5$ represents a hydrogen atom, an alkyl group having not more than 20 carbon atoms or a phenyl group.

4. An optically active compound represented by the formula (2)

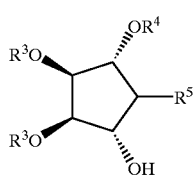

(2)

wherein $R^4$ represents a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, $R^2$ and $R^3$ jointly represent acetonide, methyl ethyl ketal or diethyl ketal, and $R^5$ represents a hydrogen atom, an alkyl group having not more than 20 carbon atoms or a phenyl, and its enantiomer represented by the formula (5)

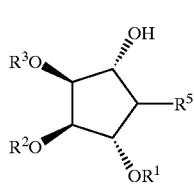

(5)

wherein $R^1$ represents a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, and R², R³ and R⁵ are as defined above.

5. An optically active compound represented by the formula (3)

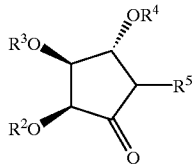

(3)

wherein R⁴ represents a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, R² and R³ jointly represent acetonide, methyl ethyl ketal or diethyl ketal, and R⁵ represents a hydrogen atom, an alkyl group having not more than 20 carbon atoms or a phenyl, and its enantiomer represented by the formula (6)

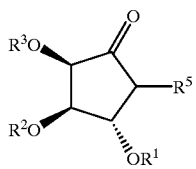

(6)

wherein R¹ represents a cumyl group, α,α-diethylbenzyl, α,α-dimethyl-p-methoxybenzyl, t-butyldimethylsilyl, trimethylsilyl, triethylsilyl, triisopropylsilyl, isopropyldimethylsilyl or ethyldimethylsilyl, and R², R³ and R⁵ are as defined above.

6. The process of claim 1, wherein R² and R³ in formula (4) jointly represent acetonide.

7. The process of claim 1, wherein R¹ and R⁴ in formula (1) each independently represent a cumyl group, α,α-diethylbenzyl, α,α-dimethyl-p-methoxybenzyl or t-butyldimethylsilyl.

8. The process of claim 1, wherein R⁵ in formula (4) is hydrogen atom or an alkyl group of 20 carbon atoms or less.

9. The process of claim 2, wherein R² and R³ in formula (7) jointly represent acetonide.

10. The process of claim 2, wherein R¹ and R⁴ in formula (1) each independently represent a cumyl group, α,α-diethylbenzyl, α,α-dimethyl-p-methoxybenzyl or t-butyldimethylsilyl.

11. The process of claim 2, wherein R⁵ in formula (7) is hydrogen atom or an alkyl group of 20 carbon atoms or less.

12. The compound of claim 3, wherein R¹ and R⁴ in formula (1) each independently represent a cumyl group, α,α-diethylbenzyl, α,α-dimethyl-p-methoxybenzyl or t-butyldimethylsilyl.

13. The compound of claim 3, wherein R² and R³ in formula (1) jointly represent acetonide.

14. The compound of claim 3, wherein R⁵ in formula (1) represents a hydrogen atom or an alkyl group of 20 carbon atoms or less.

15. The compound of claim 4, wherein R⁴ in formula (2) represents a cumyl group, α,α-diethylbenzyl, α,α-dimethyl-p-methoxybenzyl or t-butyldimethylsilyl.

16. The compound of claim 4, wherein R² and R³ in formula (2) jointly represent acetonide.

17. The compound of claim 5, wherein R⁴ in formula (3) represennts a cumyl group, α,α-diethylbenzyl, α,α-dimethyl-p-methoxybenzyl or t-butyldimethylsilyl.

18. The compound of claim 5, wherein R² and R³ in formula (3) jointly represent acetonide.

* * * * *